United States Patent
Harton (10) Patent No.: US 10,207,100 B2
(45) Date of Patent: Feb. 19, 2019

(54) INJECTION PORT WITH ARTICULATED STOPCOCK

(71) Applicant: Christopher E. Harton, Allen, TX (US)

(72) Inventor: Christopher E. Harton, Allen, TX (US)

(73) Assignee: Quest Medical, Inc., Allen, TX (US)

(*) Notice: Subject to any disclaimer, the term of this patent is extended or adjusted under 35 U.S.C. 154(b) by 0 days.

(21) Appl. No.: 13/912,670

(22) Filed: Jun. 7, 2013

(65) Prior Publication Data

US 2015/0202424 A1 Jul. 23, 2015

Related U.S. Application Data

(60) Provisional application No. 61/662,402, filed on Jun. 21, 2012, provisional application No. 61/656,567, filed on Jun. 7, 2012.

(51) Int. Cl.
*A61M 39/22* (2006.01)
*A61M 39/10* (2006.01)
*A61M 39/02* (2006.01)
*A61M 39/24* (2006.01)

(52) U.S. Cl.
CPC ........... *A61M 39/22* (2013.01); *A61M 39/10* (2013.01); *A61M 39/1055* (2013.01); *A61M 2039/027* (2013.01); *A61M 2039/0258* (2013.01); *A61M 2039/0276* (2013.01); *A61M 2039/0285* (2013.01); *A61M 2039/1033* (2013.01);

(Continued)

(58) Field of Classification Search
CPC .. A61M 39/0247; A61M 39/04; A61M 39/06; A61M 2039/0633; A61M 39/22; A61M 2039/229; A61M 39/02; A61M 2039/0205; A61M 2039/0258; A61M 2039/0285; A61M 2039/0276; A61M 2039/027; A61M 2039/064; A61M 2039/0646; A61M 2039/066; A61M 2039/0009; A61M 2039/0202; A61M 39/223; A61M 39/00

See application file for complete search history.

(56) References Cited

U.S. PATENT DOCUMENTS

| | | | | |
|---|---|---|---|---|
| 4,051,852 A | * | 10/1977 | Villari ................... | A61M 39/02 604/183 |
| 5,112,301 A | * | 5/1992 | Fenton, Jr. ............ | A61M 1/008 604/247 |

(Continued)

*Primary Examiner* — Jenna Zhang
(74) *Attorney, Agent, or Firm* — GrayRobinson, P.A.

(57) ABSTRACT

The present invention is an injection port with an articulated stopcock allowing a syringe to be connected to an IV line and, depending upon the orientation of the stopcock, allow (1) bidirectional flow of fluid through the stopcock into the IV line, (2) no flow or (3) unidirectional flow of fluid through the stopcock and into or out of the IV line. The invention is particularly useful for using a syringe for aspirating an IV line and then injecting a medicine from the syringe into the IV line. Once a syringe is connected, the invention allows one-handed manipulation of the articulated stopcock into the three orientations by simply moving the connected syringe into one of the three orientations, thereby eliminating the need for using two hands—one to operate the syringe and the other to operate the handle.

12 Claims, 10 Drawing Sheets

(52) U.S. Cl.
CPC ............ *A61M 2039/229* (2013.01); *A61M 2039/2433* (2013.01)

(56) References Cited

U.S. PATENT DOCUMENTS

| | | | | |
|---|---|---|---|---|
| 6,827,329 | B2* | 12/2004 | Mikiya | F16L 37/47 137/616.7 |
| 6,899,132 | B2* | 5/2005 | Mikiya | F16K 5/061 137/616.7 |
| 8,602,058 | B1* | 12/2013 | Del Castillo | A61M 39/223 137/625.41 |
| 2002/0062872 | A1* | 5/2002 | Makishima | F16L 37/47 137/616.7 |
| 2003/0122095 | A1* | 7/2003 | Wilson | A61B 5/0215 251/12 |
| 2005/0087241 | A1* | 4/2005 | Kohda | F16L 37/23 137/614.03 |
| 2007/0235674 | A1* | 10/2007 | Vangsness | A61M 39/045 251/149.2 |

* cited by examiner

INJECTION PORT WITH ARTICULATED STOPCOCK

CROSS-REFERENCE TO RELATED INVENTIONS

This application claims the benefit of provisional application No. 61/656,567, filed Jun. 7, 2012, and 61/662,402, filed Jun. 21, 2012, the disclosures of both of which are incorporated by reference herein.

BACKGROUND OF THE INVENTION

Field of the Invention

This invention relates to intravenous (IV) systems used in the medical industry. More particularly, this invention relates to IV stopcocks.

Description of the Background Art

Presently, there exist many components to intravenous (IV) systems designed to deliver medications to a patient or to draw blood from the patient. Historically, ports in IV systems allowed a medical practitioner to access the IV system via a hypodermic needle to administer fluids to the patient or to withdraw blood from the patient. In more recent years, such ports have been supplanted by needleless access ports containing a swabable valve with a Luer fitting that allows the medical practitioner to directly connect the syringe to the needleless access port without the use of a hypodermic needle. Needleless access ports are universally preferred over ports that are accessed by means of a hypodermic needle to eliminate the risk of inadvertent needle pricks to the medical practitioner that could otherwise result in the spreading of a disease, particularly AIDS.

In many IV applications, it is desirous to use stopcocks to selectively control the flow of medications from a syringe into the IV line for delivery to the patient and to permit or not permit retrograde flow from the patient to the IV line to the syringe. Typical stopcocks comprise one port having a swabable valve to which the syringe is connected and then two other valved ports operated by a twist handle that may be rotated to (1) allow fluid flow to one port, (2) allow fluid flow to another port or (3) to preclude fluid flow altogether. Hence, stopcocks are in widespread use in the medical industry.

Conventional stopcocks typically comprise a three-port device with a rotatable handle that operatively allows fluid flow through the stopcock depending on the orientation of the handle. With a syringe connected to a first port, the handle may be oriented in one position to permit fluid flow through a second port. If the position of the syringe attached to the first port changes the fluid flow is allowed through a different port. Typically, the handle is marked with indicia, such as arrows or ridges, to visually indicate the direction of permissible fluid flow versus when fluid flow is blocked or "checked."

Many stopcocks are cumbersome to operate, some requiring two-handed operation. Others are complicated and costly to manufacture.

Therefore, it is an object of this invention to provide an improvement which overcomes the aforementioned inadequacies of the prior art and provides an improvement which is a significant contribution to the advancement of the stopcock art.

Another object of this invention is to provide a stopcock that is simple in design and cost-effective to manufacture.

Another object of this invention is to provide a stopcock that is easy to operate with one-hand.

Another object of this invention is to provide a stopcock that is particularly useful for using a syringe for aspirating an IV line and then injecting a medicine from the syringe into the IV line.

The foregoing has outlined some of the pertinent objects of the invention. These objects should be construed to be merely illustrative of some of the more prominent features and applications of the intended invention. Many other beneficial results can be attained by applying the disclosed invention in a different manner or modifying the invention within the scope of the disclosure. Accordingly, other objects and a fuller understanding of the invention may be had by referring to the summary of the invention and the detailed description of the preferred embodiment in addition to the scope of the invention defined by the claims taken in conjunction with the accompanying drawings.

SUMMARY OF THE INVENTION

For the purpose of summarizing this invention, this invention comprises an injection port with an articulated stopcock allowing a syringe to be connected to and IV line and, depending upon the orientation of the stopcock, allow (1) bidirectional flow of fluid through the stopcock into the IV line, (2) no flow or (3) unidirectional flow of fluid through the stopcock and into or out of the IV line. The invention is particularly useful for using a syringe for aspirating an IV line and then injecting a medicine from the syringe into the IV line. Importantly, once a syringe is connected, the invention allows one-handed manipulation of the articulated stopcock into the three orientations by simply moving the connected syringe into one of the three orientations, thereby eliminating the need for using two hands—one to operate the syringe and the other to operate the handle.

The foregoing has outlined rather broadly the more pertinent and important features of the present invention in order that the detailed description of the invention that follows may be better understood so that the present contribution to the art can be more fully appreciated. Additional features of the invention will be described hereinafter which form the subject of the claims of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a fuller understanding of the nature and objects of the invention, reference should be had to the following detailed description taken in connection with the accompanying drawings in which.

Similar reference characters refer to similar parts throughout the several views of the drawings.

DETAILED DESCRIPTION OF THE PREFERRED EMBODIMENT

The injection port and articulated stopcock 10 of the invention comprises a generally circular cylindrical housing 12 including a generally semi-spherical socket 14. A swabable valve 16 is positioned within the socket 14 to articulate therein among a bidirectional flow position (FIG. 1), and off position (FIG. 2) and a unidirectional flow position (FIG. 3). Hence, the articulation of the swabable valve 16 serves as a stopcock.

The housing 12 includes an axial passageway 12A that extends axially through the housing 12. The housing 12 further includes a bypass passageway 12B extending through the side of the housing 12 parallel to the axial passageway 12A. Both the axial passageway 12A and the bypass passageway 12B extend into a cavity 12C formed in the distal end of the housing 12. The axial passageway 12A extends into the bottom center of the socket 14 whereas the bypass passageway extends into the side of the socket 14.

The swabable valve 16 comprises a valve body 16B having a generally semi-spherical bottom 16S that is configured and dimensioned to fit into the socket 14 of the housing 12. An outlet 16O is formed through the semi-spherical bottom 16S of the valve body 16B. The valve body 16B is composed of an upper component and a lower component connected together at joint line 16J by sonic welding, solvent bonding or the like.

The upper periphery of the housing 12 comprises a cut-out relief 12R angled at approximately 90 degrees to allow the swabable valve 12 to rotate therein from an aligned, axial position to an angled position generally transverse to the axis of the housing 12. The spherical bottom 16S of the swabable valve 16 comprises a pair of axles 16A extending from diametrically opposed portions of the spherical bottom 16S. The axles 16A are rotatably journalled within corresponding axel holes 12AH that serve as journal bearings to allow the swabable valve to 16 to rotate within the housing 12.

The swabable valve 16 further comprises a conventional valve element 16E that remains closed until accessed by a Luer fitting of a conventional syringe. The valve element 16E preferably comprises the type of valve element shown and described in U.S. Pat. No. 6,651,956, the disclosure of which is hereby incorporated by reference herein.

Figure 1A:
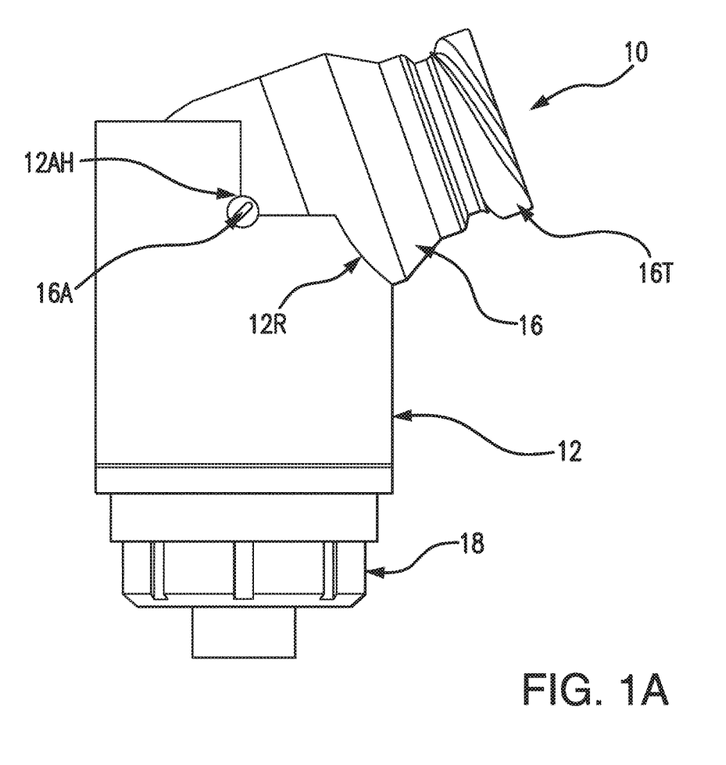
FIG. 1A is a side elevational view of the injection port with its articulated stopcock oriented for bidirectional flow and FIG. 1B is a cross-sectional view thereof.
Figure 1B:
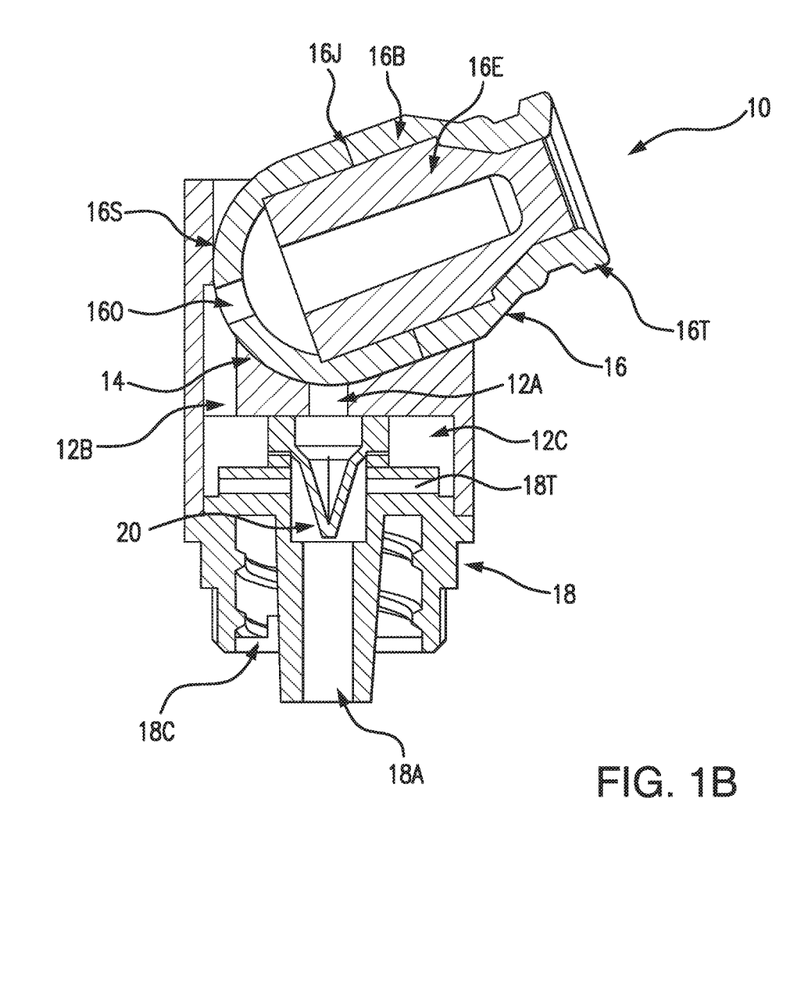
Figure 2A:
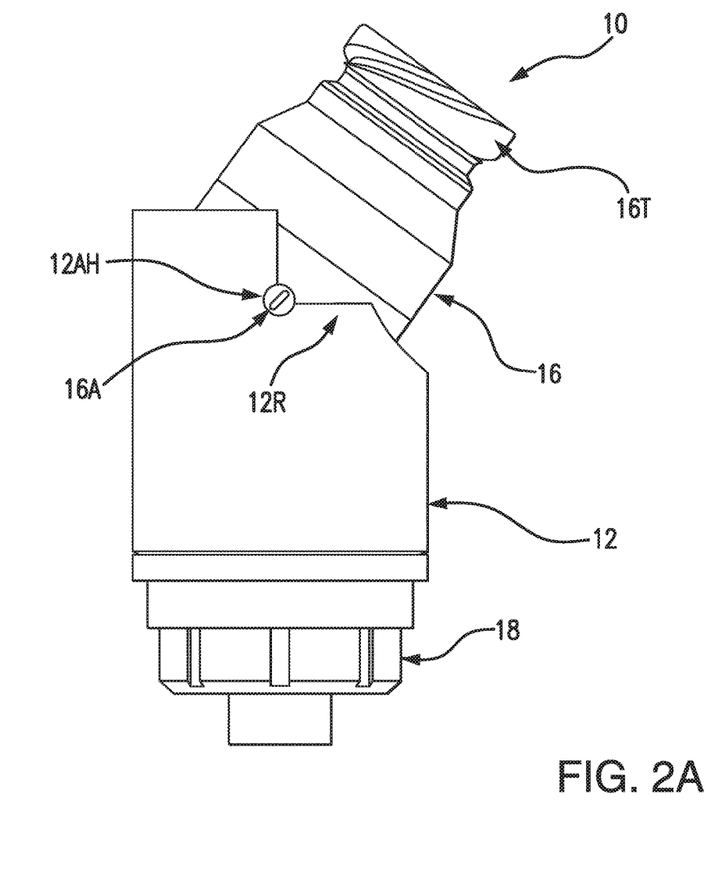
FIG. 2A is a side elevational view of the injection port with its articulated stopcock oriented for no flow and FIG. 2B is a cross-sectional view thereof.
Figure 2B:
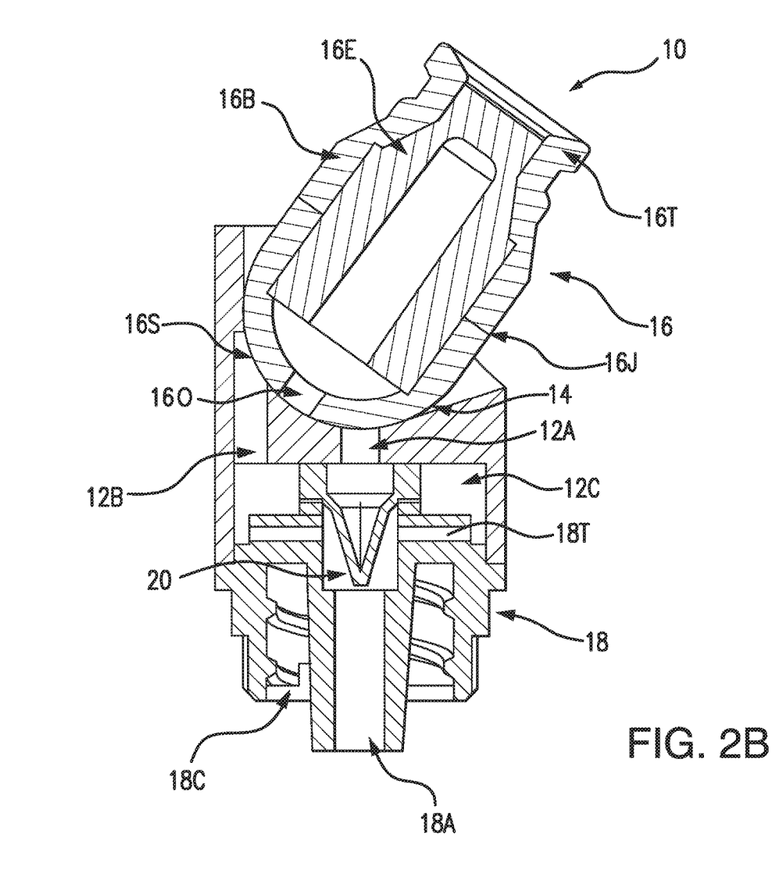
Figure 3A:
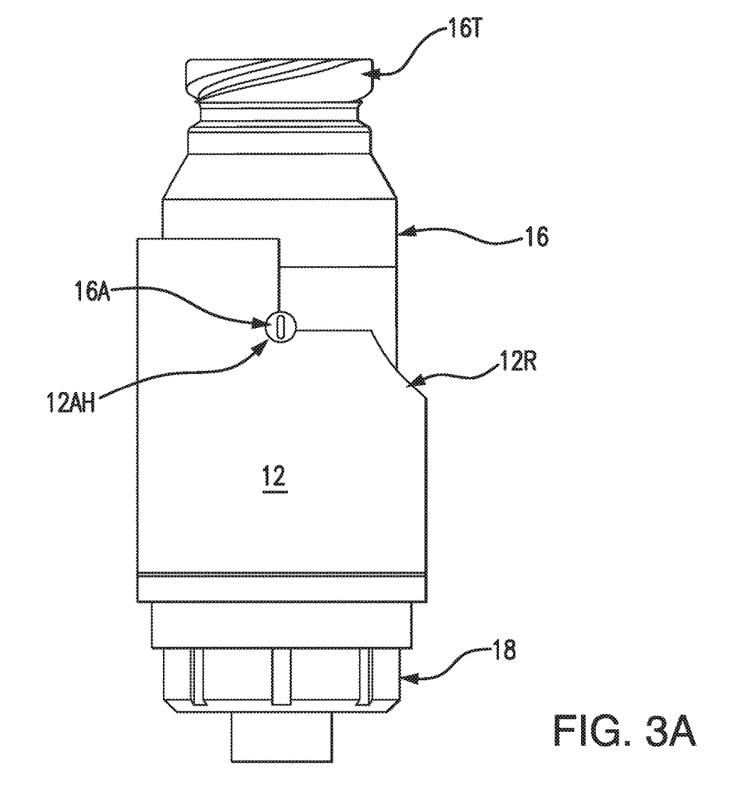
FIG. 3A is a side elevational view of the injection port with its articulated stopcock oriented for unidirectional flow and FIG. 3B is a cross-sectional view thereof.
Figure 3B:
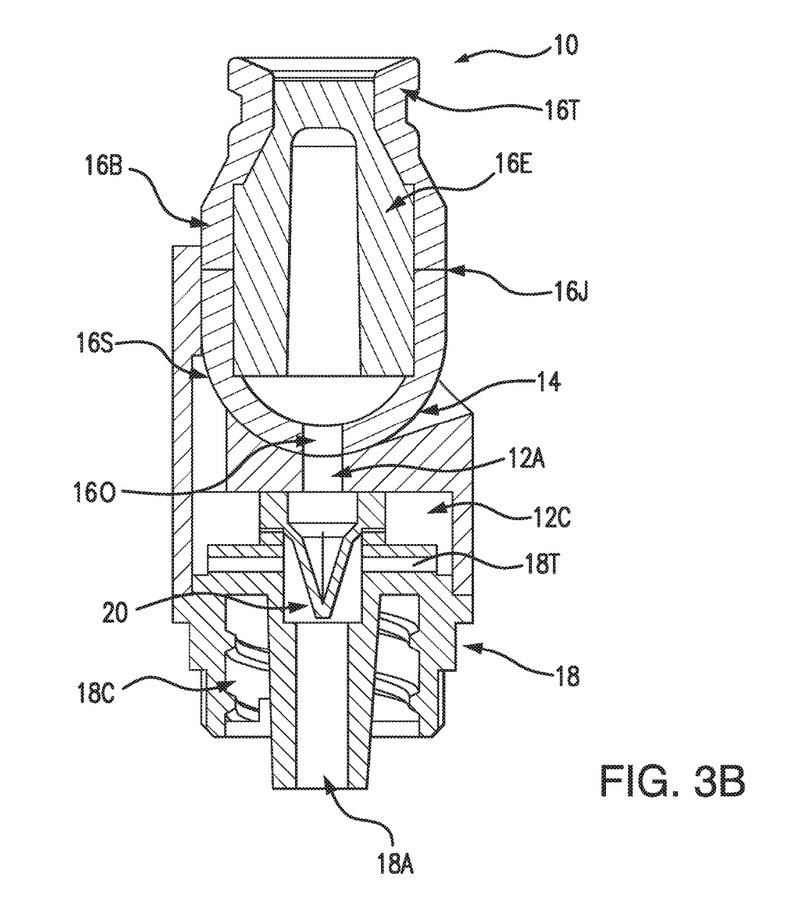
Figure 4:
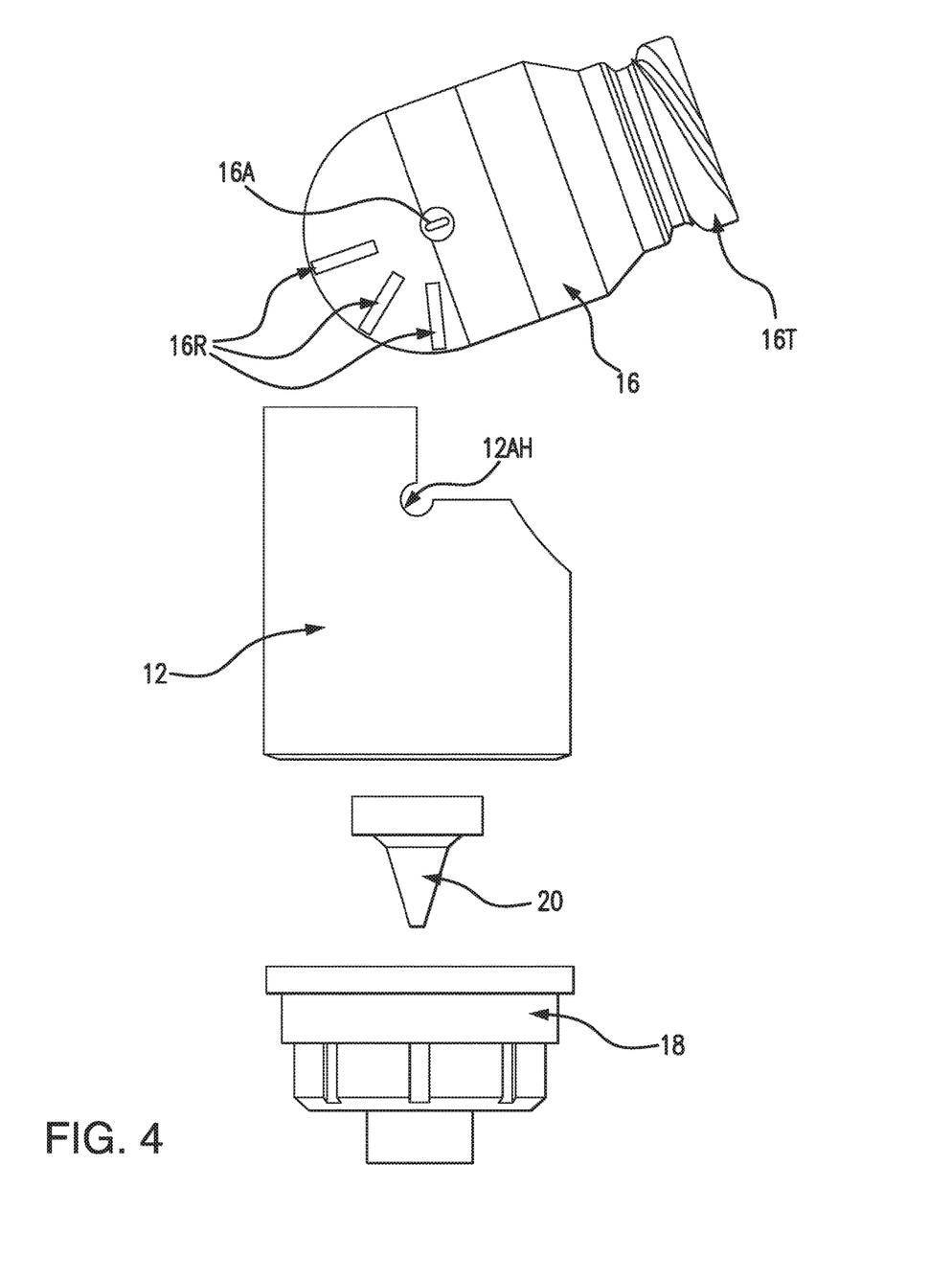
FIG. 4 is an exploded view of FIG. 1A.

The axial passageway 12A and the bypass passageway 12B of the housing 12 are arranged relative to the outlet 16O of the valve body 16B such that (1) when the swabable valve 16 is oriented as shown in FIG. 1, its outlet 16O is in alignment with the bypass passageway 12B, (2) when the swabable valve 16 is oriented as shown in FIG. 2, its outlet 16O is sealed against the semi-spherical wall of the socket 14 and (3) when the swabable valve 16 is oriented as shown in FIG. 3, its outlet 16O is in alignment with the axial passageway 12A. Hence, the respective orientations of the swabable valve 16 determine whether the swabable valve 16 is in fluid communication with the bypass passageway 12B (FIG. 1), is sealed off (FIG. 2) or is in fluid communication with the axial passageway 12A (FIG. 3).

A connector 18 is sealingly fitted to the distal end of the housing 12 so as to encapsulate its cavity 12C. Connector 18 comprises an axial passageway 18A and a transverse passageway 18T. A one-way duck bill valve 20 is positioned within the axial passageway 18A of the connector 18. Preferably the one-way valve 20 comprises a duck bill valve 20.

Figure 5:
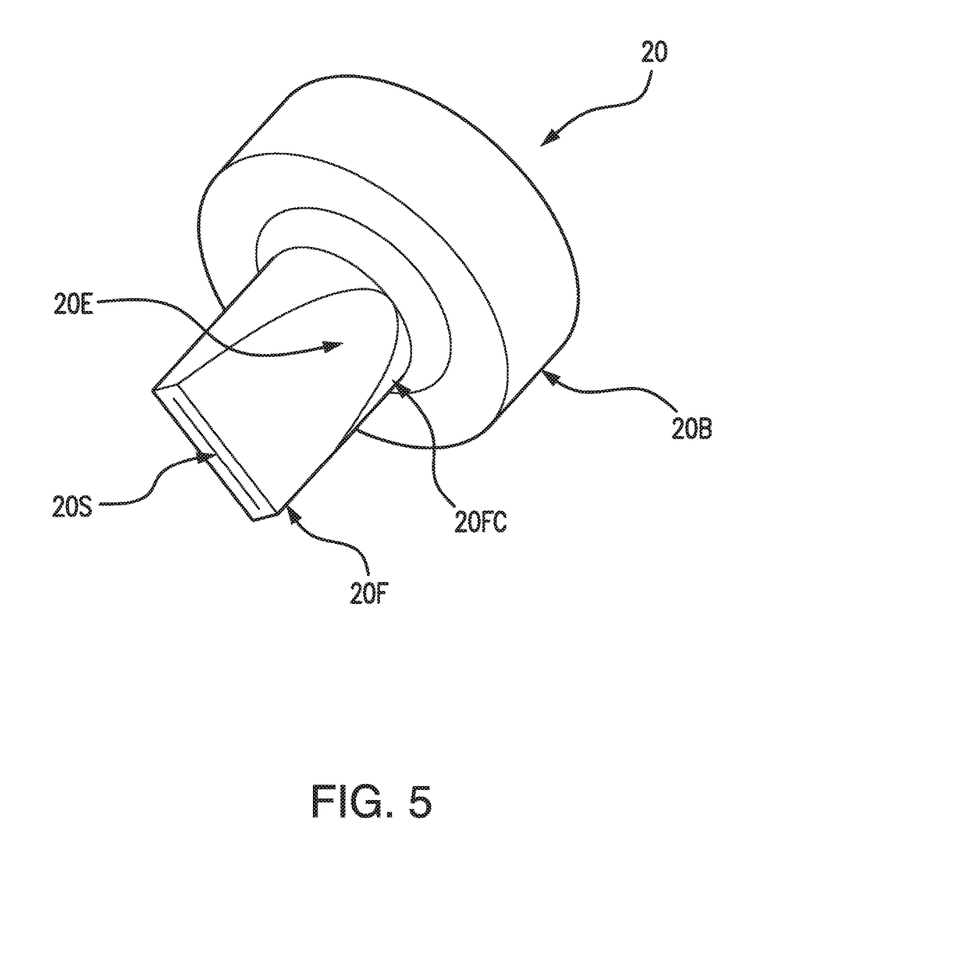
FIG. 5 is a bottom perspective view of the duck bill valve.

As shown in FIG. 5, the duck bill valve 20 comprises a generally circular-cylindrical body 20B dimensioned to sealingly fit between the proximal end of the axial passageway 18A of the connector 18 and about the axial passageway 12A of the housing 12. The duck bill valve 20 further includes an elastomeric valve element 20E whose side walls extend from a generally frustoconical configuration 20FC to a flattened configuration 20F having a slit 20S. The inherent elastomeric properties of the duck bill 20 constantly urge the slit 20S closed to check any fluid flow from the axial passageway 18A of the connector 18 into the duck bill valve 20 yet allows the slit 18S to separate to allow fluid flow out of the duck valve 20 into the axial passageway 18A. Hence, the duck bill valve 20 functions as a one-way check valve. Consequently, while both the axial passageway 18A and transverse passageway 18T of the connector 18 are connected in fluid communication with the cavity 12C of the valve body 12B, the flow of fluid in the axial passageway 18A is kept one directional by virtue of the duck bill valve 20 being positioned in the axial passageway 18A. Similarly, while the outlet 16O is in fluid communication with the bypass valve 12B flowing into cavity 12C and not in communication with axial passageway 12A, fluid may flow in both directions along the transverse passageway 18T without being stopped by the duck bill valve 20.

Preferably the proximal end of the swabable valve 16 comprises a female connector, more preferably a female Luer lock connector having external threads 16T for threadably receiving a corresponding male Luer lock connector of a syringe or other medical device. Preferably, the distal end of the connector 18 comprises a male connector, more preferably a male Luer lock connector having an internally-threaded collar 18C for threadably receiving a corresponding female Luer lock connector of a medical device such as a female Luer access port of an IV line.

Depending on the orientation of the swabable valve 16, there are three modes of operation: (1) fluid flow is bidirectional when the swabable valve 16 is oriented in the position shown in FIG. 1 with its outlet 16O in alignment with the bypass passageway 12B, allowing for fluid flow through cavity 12C, through the transverse passageway 18T and out the distal end of the connector 18 (2) fluid flow is blocked in either direction when the swabable valve 16 is oriented in the position shown in FIG. 2 with its outlet 16O sealed off by the wall of the socket 14 (3) fluid flow is one directional when the swabable valve 16 is oriented in the position shown in FIG. 3 with its outlet 16O in alignment with the axial passageway 12A of the housing 12, allowing for fluid flow through the one-way duck bill valve 20, through the axial passageway 18A of the connector and out the distal end of the connector 18 (any reverse flow being checked by the one-way valve 20).

Figure 6A:
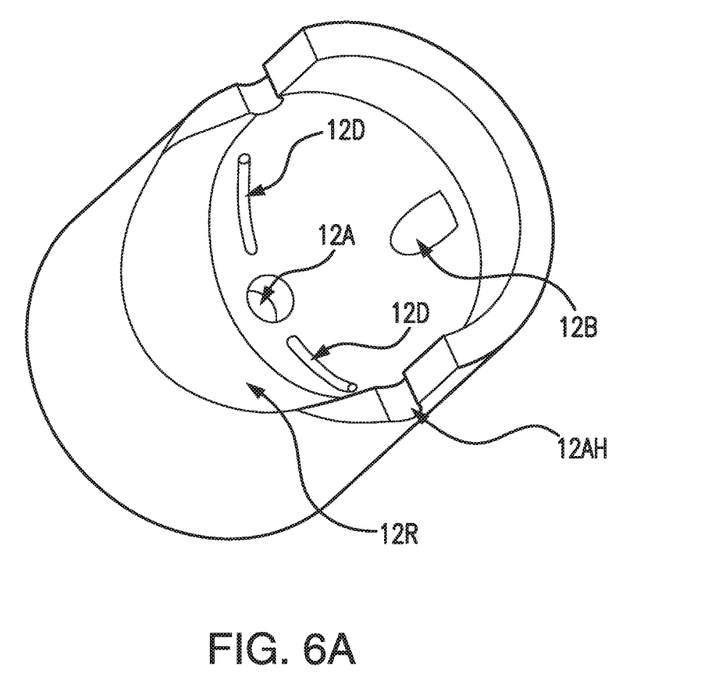
FIG. 6A is a perspective view of the semi-spherical surface of the socket showing the ridges and FIG. 6B is a perspective view of the semi-spherical surface of the swabable valve showing the three rows of detents that engage the ridges to locate the three orientations of the articulated stopcock.
Figure 6B:
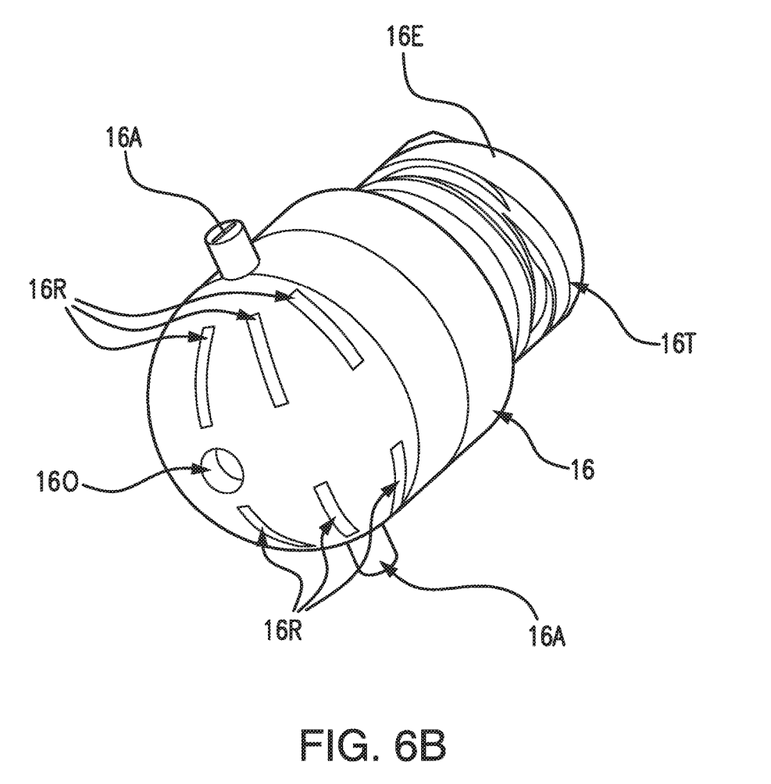

As shown in FIGS. 6A & 6B, the three orientations of the swabable valve 16 may be more positively located by incorporating a row of ridges 16R formed in the socket 16 that releasably engage into three rows of detents 12D formed into the spherical bottom 16S of the body 16B of the valve 16.

The present disclosure includes that contained in the appended claims, as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention.

Now that the invention has been described,

What is claimed is:

1. A fluid control device; comprising in combination:
a housing having a longitudinal axis including a socket and a connector having an axial passageway extending along the longitudinal axis of the housing;
an articulated member including a swabable valve positioned within said socket to articulate therein relative to said housing, said articulated member including said swabable valve being articulated among an axial unidirectional flow position allowing unidirectional flow with said axial passageway of said connector, a first angled off position precluding any flow with said axial passageway of said connector, and a second angled bidirectional flow position allowing bidirectional flow with said axial passageway of said connector, whereby the articulated orientation of said articulated member including the swabable valve relative to said housing determines unidirectional, off, and bidirectional modes of operation.

2. The fluid control device as set forth in claim 1, wherein said housing includes a bypass passageway extending non-axially relative to the longitudinal axis through a side of said housing and extending parallel to said axial passageway for fluid communication with an outlet formed in said articulated member when said articulated member is articulated in said axial unidirectional flow position allowing unidirectional flow with said axial passageway of said connector or in said second angled bidirectional flow position allowing bidirectional flow with said axial passageway of said connector, wherein both said axial passageway and said bypass passageway extend into a cavity formed in a distal end of said housing with said axial passageway extending into a bottom center of said socket and said bypass passageway extending into a side of the socket and wherein said cavity is connected in fluid communication with said axial passageway of said connector.

3. The fluid control device as set forth in claim 2, wherein said articulated member comprises a valve body configured and dimensioned to fit into said socket of said housing.

4. The fluid control device as set forth in claim 3, wherein said socket and said valve body comprise complementary generally semi-spherical configurations.

5. The fluid control device as set forth in claim 4, wherein said valve body is composed of an upper component and a lower component connected together at a joint line.

6. The fluid control device as set forth in claim 5, wherein an upper periphery of said housing comprises a cut-out relief to allow said articulated member to rotate therein to said second angled bidirectional flow position.

7. The fluid control device as set forth in claim 6, wherein said lower component of said valve body comprises a pair of axles extending from diametrically opposed portions of said bottom center; said pair of axles being rotatably journalled within corresponding axle holes in said housing to allow said articulated member to rotate within said socket of said housing.

8. The fluid control device as set forth in claim 7, wherein said connector comprises a transverse passageway fluidly connected to said cavity.

9. The fluid control device as set forth in claim 8, further including a one-way valve positioned upstream of said transverse passageway within said cavity between an axial passageway of said housing allowing only unidirectional flow with said axial passageway of said connector.

10. The fluid control device as set forth in claim 9, wherein said one-way valve comprises a duck bill valve.

11. The fluid control device as set forth in claim 8, wherein a proximal end of said swabable valve comprises a female connector and a distal end of said connector comprises a male connector.

12. The fluid control device as set forth in claim 11, wherein said female connector and said male connector comprise complementary Luer connectors.

* * * * *

UNITED STATES PATENT AND TRADEMARK OFFICE
CERTIFICATE OF CORRECTION

PATENT NO. : 10,207,100 B2
APPLICATION NO. : 13/912670
DATED : February 19, 2019
INVENTOR(S) : Christopher E. Harton Page 1 of 1

It is certified that error appears in the above-identified patent and that said Letters Patent is hereby corrected as shown below:

In the Detailed Description of the Preferred Embodiment

Column 3, Lines 34, 57, 59, 62 and 64, please delete "160" and insert --16O--.

Signed and Sealed this
Sixteenth Day of July, 2019

Andrei Iancu
*Director of the United States Patent and Trademark Office*